US008293791B2

(12) United States Patent
McCullough et al.

(10) Patent No.: US 8,293,791 B2
(45) Date of Patent: Oct. 23, 2012

(54) METHOD OF NEUROPROTECTION BY PHARMACOLOGICAL INHIBITION OF AMP-ACTIVATED PROTEIN KINASE

(75) Inventors: Louise D. McCullough, Baltimore, MD (US); Jill Sturdivant, Chapel Hill, NC (US); Gabriele V. Ronnett, Baltimore, MD (US)

(73) Assignees: FASgen, LLC, Baltimore, MD (US); Johns Hopkins University, Baltimore, MD (US)

( * ) Notice: Subject to any disclaimer, the term of this patent is extended or adjusted under 35 U.S.C. 154(b) by 831 days.

(21) Appl. No.: 10/593,710

(22) PCT Filed: Mar. 23, 2005

(86) PCT No.: PCT/US2005/009797
§ 371 (c)(1),
(2), (4) Date: Feb. 9, 2009

(87) PCT Pub. No.: WO2005/092068
PCT Pub. Date: Oct. 6, 2005

(65) Prior Publication Data
US 2009/0137665 A1 May 28, 2009

Related U.S. Application Data

(60) Provisional application No. 60/556,000, filed on Mar. 24, 2004.

(51) Int. Cl.
*A61K 31/19* (2006.01)
*A61K 31/136* (2006.01)
*A61K 31/192* (2006.01)
*A61K 31/196* (2006.01)

(52) U.S. Cl. .................. 514/557; 514/567; 514/649

(58) Field of Classification Search .................. None
See application file for complete search history.

(56) References Cited

U.S. PATENT DOCUMENTS

| 5,981,575 | A | 11/1999 | Kuhajda et al. |
| 6,423,705 | B1 | 7/2002 | Tracey et al. |
| 2002/0099075 | A1 | 7/2002 | Tracey et al. |
| 2009/0137665 | A1 | 5/2009 | McCullough et al. |

FOREIGN PATENT DOCUMENTS

| WO | WO 01/23399 | 4/2001 |
| WO | 2005/092068 | 10/2005 |
| WO | WO 2005/092068 A2 | 10/2005 |

OTHER PUBLICATIONS

Kim Y. K. et al., "Expression of FAS with Hypothalamic Neurons: a Model for Decreased Food Intake after C75 treatment," *Endocrinol Metab.* 283, E867-E879 (2002).
Leon J. et al., "Modulation of Rat Striatal Glutamatergic Response in Search for New Neuroprotective Agents: Evaluation of Melatonin and Some Kynurenine Derivatives," *Brain Research Bulletin*, 45, 525-530 (2003).
Sheng R. et al., "EDT, a Tetrahydroacridine Derivative Inhibits Cerebral Ischemia and Protects Rat Cortical Neurons Against Glutamate-Induced Cytotoxicity," *Acta Pharmacol Sin* 24(5) 390-393 (May 2003).
Carling, D., "The AMP-Activated Protein Kinase Cascade—a Unifying System for Energy Control," *Trends in Biochemical Sciences*, 29(1) 18-24 (Jan. 2004).
Witters, L., et al., "Insulin Activation of Acetyle-CoA Carboxylase Accompaned by Inhibition of the 5'-AMP-Activated Protein Kinase," *The J. of Biol. Chem.*, 267(5), 2864-2867 (Feb. 1992).
Zhihong, H., et al., "Effects of Cerebral Ischemia in Mice Deficient in Neuronal Nitric Oxide Synthase," *Science* 265, 1883-1885 (Sep. 1994).
Hawley, S. et al., "Characterization of the AMP-activated Protein Kinase Kinase from Rat Liver and Identification of Theronine 172 as the Major Site at Which it Phosphorylates AMP-activated Protein Kinase," *J. of Biol. Chem.* 271(44), 27879-27887 (Nov. 1996).
Hardie, D. G. et al., "AMP-Activated Protein Kinase: an Ultrasensitive system for Monitoring Cellular Energy Charge," *Biochem J.* 338, 717-722 (1999).
McCullough, L. et al., Neuroprotective Function of the $PGE_2$ EP2 Receptor in Cerebral Ischemia, *J. of Neuroscience* 24(1) 257-268 (Jan. 2004).
McCullough, L. et al. "Postischemic Estrogen Reduces Hypoperfusion and Secondary Ischemia After Experimental Stroke" *Stroke* 32, 796-802 (2001).
Zhou, et al., "Role of AMP-activated Protein Kinase in Mechanism of Metformin Action," *J. of Clinical Investigation* 108(8) 1167-1174 (Oct. 2001).
Corton, et al., "5-A Minoimidazole-4-Carboxamide Ribonucleoside a Specific Method for Activating AMP-Activated Protein Kinase in Intact Cells?" *Eur J. Biochem.* 229, 558-565 (1995).
Almeida, A. et al. "Nitric Oxide Switches on Glycolysis Through the AMP Protein Kinase and 6-Phosphofructo-2-Kinase Pathway," *Nature Cell Bio.* 6, 45-51 (Jan. 2004).
Hardie et al., "A Neural Protection Racket: AMPK and the $GABA_B$ Receptor", *Neuron*, 53:159-162 (2007).

(Continued)

*Primary Examiner* — Robert C Hayes
(74) *Attorney, Agent, or Firm* — FASgen, LLC

(57) ABSTRACT

A method of neuroprotection which comprises administration of an AMPK inhibitor to a patient who is experiencing or has experienced a stroke, the compound being an AMPK inhibitor. Treatments with these agents significantly reduce the size of infarcts, and therefore minimize the loss of brain tissue and neurons. Thus, function can be preserved after stroke or ischemic injury in the brain. Similarly, neuronal loss can be minimized in degenerative diseases that cause neuronal compromise by perturbing energy utilization and availability in neurons.

6 Claims, 10 Drawing Sheets

OTHER PUBLICATIONS

Beauloye et al., "Insulin antagonizes AMP-activated protein kinase activation by ischemia or anoxia in rat hearts, without affecting total adenine nucleotides," *FEBS Letters*, 505:348-352 (2001).

Culmsee et al., "AMP-activated protein kinase is highly expressed in neurons in the developing brain and promotes neuronal survival following glucose deprivation," *J. Mol. Neurosci.*, 17(1):45-58 (2001) (abstract only).

Eliasson et al., "Poly(ADP-ribose) polymerase gene disruption renders mice resistant to cerebral ischemia," *Nature Medicine*, 3(10):1089-1095 (1997).

Gadalla et al., "AICA riboside both activates AMP-activated protein kinase and competes with adenosine for the nucleoside transporter in the CA1 region of the rat hippocampus," *Journal of Neurochemistry*, 88:1272-1282 (2004).

International Search Report, International Application No. PCT/US05/09797 (published as WO 2005/092068), dated Jun. 20, 2007.

Kim et al., "C75, a Fatty Acid Synthase Inhibitor, Reduces Food Intake via Hypothalamic AMP-Activated Protein Kinase," *The Journal of Biological Chemistry*, 279(19):19970-19976 (2004).

Kuramoto et al., "Phospho-Dependent Functional Modulation of $GABA_B$ Receptors by the Metabolic Sensor AMP-Dependent Protein Kinase," *Neuron*, 53:233-247 (2007).

Küry et al., "Transcriptional response to circumscribed cortical brain ischemia: spatiotemporal patterns in ischemic vs. remote non-ischemic cortex," *European Journal of Neuroscience*, 19:1708-1720 (2004).

Landree et al., "C75, a Fatty Acid Synthase Inhibitor, Modulates AMP-Activated Protein Kinase to Alter Neuronal Energy Metabolism," *The Journal of Biological Chemistry*, 279(5):3817-3827 (2004).

Mangano, "Effects of Acadesine on Myocardial Infarction, Stroke, and Death Following Surgery: A Meta-analysis of the 5 International Randomized Trials," *JAMA*, 277(4):325-332 (1997).

McCullough et al., "Aromatase Cytochrome P450 and Extragonadal Estrogen Play a Role in Ischemic Neuroprotection," *The Journal of Neuroscience*. 23(25):8701-8705 (2003).

Russell et al., "AMP-activated protein kinase mediates ischemic glucose uptake and prevents postischemic cardiac dysfunction, apoptosis, and injury," *The Journal of Clinical Investigation*, 114(4):495-503 (2004).

Saha et al., "Pioglitazone treatment activates AMP-activated protein kinase in rat liver and adipose tissue in vivo," *Biochemical and Biophysical Research Communications*, 314:580-585 (2004).

Xing et al., "Glucose Metabolism and Energy Homeostasis in Mouse Hearts Overexpressing Dominant Negative $\alpha 2$ Subunit of AMP-activated Protein Kinase," *The Journal of Biological Chemistry*, 278(31):28372-28377 (2003).

METHOD OF NEUROPROTECTION BY PHARMACOLOGICAL INHIBITION OF AMP-ACTIVATED PROTEIN KINASE

This is a nationalization of PCT/US2005/009797 filed 23 Mar. 2005 and published in English, claiming the benefit of US Provisional Application 60/556,000 filed 24 Mar. 2004.

BACKGROUND OF THE INVENTION

Stroke, defined as an abnormality in brain function resulting from disruption of cerebral circulation, is one of the leading causes of death in the U.S. Even when a stroke does not result in death, the costs it imposes on the victim may include serious physical and emotional damage, which may result in loss of productivity. These costs stem from the tremendous damage done to the victim's brain by the stroke. With a reduction in oxygen and glucose, cells display a rapid disruption of protein synthesis, depletion of intracellular energy stores, destabilization of the cell membrane, and activation of the NMDA receptor, leading to excitotoxic and oxidative cell damage in the brain. In an attempt to survive and repair the oxidative damage and return the cell to homeostasis, numerous compensatory energy-consuming processes are activated. However, over-activation of these pathways can deleterious, further depleting cellular energy, and resulting in further brain damage. Such brain damage is, generally, irreversible. Accordingly, a method of protecting brain tissue from damage during a stroke (neuroprotection) would be tremendously important.

AMP-activated protein kinase (AMPK), a member of a metabolite-sensing protein kinase family, is a known sensor of peripheral energy balance (Carting D., "The AMP-activated protein kinase cascade—a unifying system for energy control." *Trends Biochem Sci* 6:314 (2): 580-585, 2004.) AMPK is a heterotrimeric protein composed of a catalytic $\alpha$ subunit ($\alpha 1$ or $\alpha 2$), and 2 regulatory subunits ($\beta$ and $\gamma$). AMPK is phosphorylated and activated when cellular energy levels are low. AMPK in turn regulates cellular metabolism and chronically regulates gene expression to restore ATP levels. Increases in the AMP/ATP ratio, changes in cellular pH and redox status, and increases in the creatine/phosphocreatine ratio are known to activate AMPK (Hardie D G, Salt I P, Hawley S A, Davies S P, "AMP-activated protein kinase: an ultrasensitive system for monitoring cellular energy charge," *Biochem J* 338:717-22, 1999; Hawley S A, Davison M, Woods A, et al., "Characterization of the AMP-activated protein kinase kinase from rat liver and identification of threonine 172 as the major site at which it phosphorylates AMP-activated protein kinase," *J Biol Chem* 271:27879-87, 1996.) AMPK increases fatty acid oxidation and restricts fatty acid synthesis in an attempt to augment ATP levels in energy-depleted cells. However, in neurons that have a restricted capacity for fatty acid oxidation, this effect could be deleterious (Almeida A, Moncada S, Bolanos J P, "Nitric oxide switches on glycolysis through the AMP protein kinase and 6-phosphofructo-2-kinase pathway," *Nature Cell Biology* 6:45-51, 2004).

Inhibition of fatty acid synthase (FAS), the enzyme responsible for the de novo synthesis of palmitate, with C75, a synthetic FAS inhibitor disclosed in U.S. Pat. No. 5,981,575 (incorporated herein by reference), increases ATP levels in a number of cell types, including neurons. AMPK is highly expressed in neurons in the hypothalamus, where it appears to play a role in the regulation of food intake. Hypothalamic phosphorylated AMPK (pAMPK) is increased with starvation; C75 treatment inactivates and dephosphorylates AMPK, and induces profound anorexia.

The consequences of AMPK activation in neurons that do not have access to energy supplies is unknown. Until the present invention, it has been unclear whether AMPK activation during stress was protective or damaging. There have been no prior studies examining the role of AMPK in stroke.

SUMMARY OF THE INVENTION

Applicants have invented a method of neuroprotection which comprises administering a compound to a patient who is experiencing or has experienced a stroke, the compound being an AMPK inhibitor.

Treatments with these agents significantly reduce the size of infarcts, and therefore minimize the loss of brain tissue and neurons. Thus, function can be preserved after stroke or ischemic injury in the brain. Similarly, neuronal loss can be minimized in degenerative diseases that cause neuronal compromise by perturbing energy utilization and availability in neurons.

DETAILED DESCRIPTION OF THE INVENTION

Figure 1:
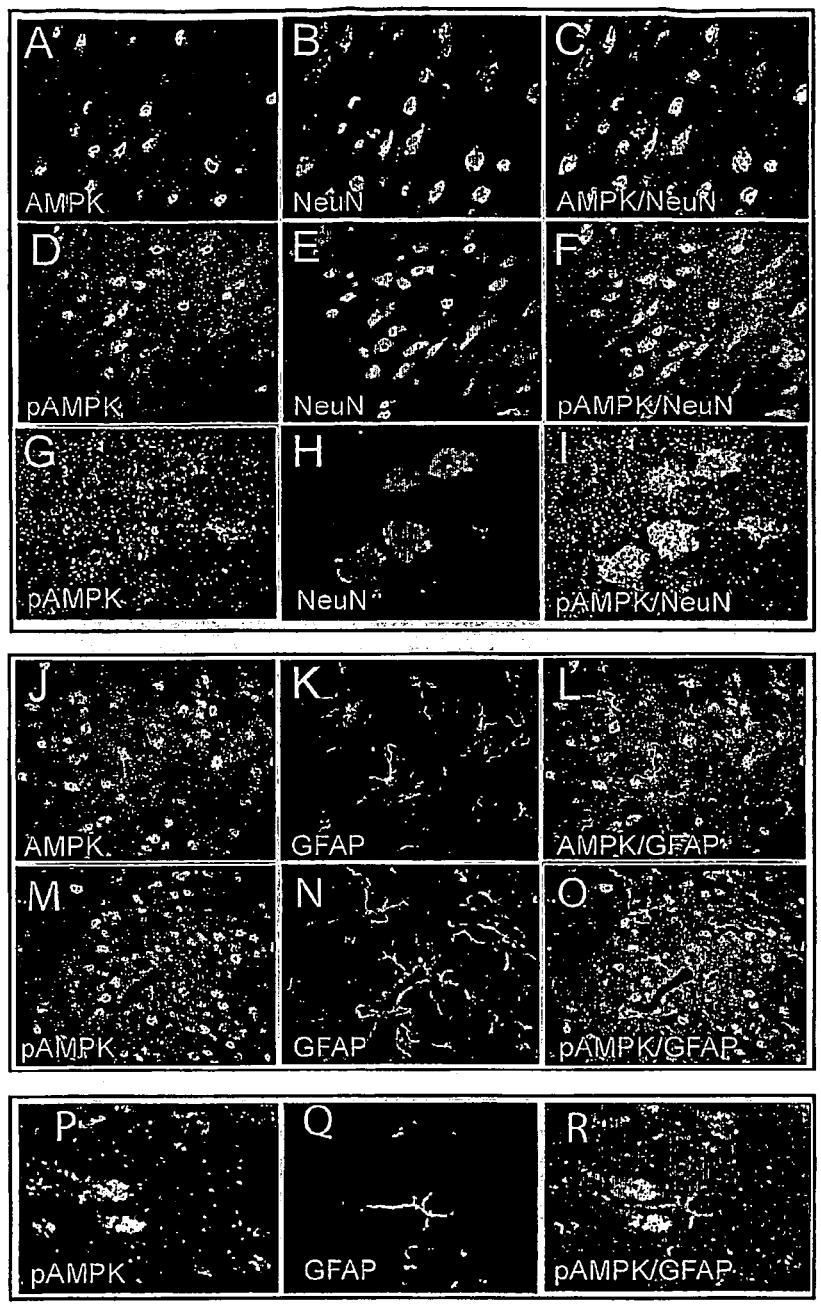
FIG. 1—Immunohistochemical localization of AMPK and pAMPK in ischemic mouse brain.

By "neuroprotection," we mean protecting brain cells, preferably neurons, from permanent damage caused by a stroke during and after the stroke.

By "stroke," we mean an abnormality in brain function resulting from disruption of cerebral circulation.

By "AMPK inhibitor," we mean a compound which inhibits AMPK as determined by the method described by Witters, et al., *Journal of Biological Chemistry*, 267, pp. 2864-2867 (1992).

Preferably, the AMPK inhibitor is selected from a compound which is not a peptide or other biological (or biologically-derived) material, but is a small molecule.

The compositions of the present invention can be presented for administration to humans and other animals in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions. As used in this specification, the terms "pharmaceutical diluent" and "pharmaceutical carrier," have the same meaning. For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms or oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

The subject is preferably a mammal, more preferably a human.

Dose and duration of therapy will depend on a variety of factors, including (1) the subject's age, body weight, and organ function (e.g., liver and kidney function); (2) the nature and extent of the disease process to be treated, as well as any existing significant co-morbidity and concomitant medications being taken, and (3) drug-related parameters such as the route of administration, the frequency and duration of dosing necessary to effect a cure, and the therapeutic index of the drug. In general, does will be chosen to achieve serum levels of 1 ng/ml to 100 ng/ml with the goal of attaining effective concentrations at the target site of approximately 1 µg/ml to 10 µg/ml.

Ideally, the compound will be administered as soon as possible following the onset of the stroke.

Prior to this invention, the role of neuronal metabolism in the response to brain injury was unknown. Without wishing to be bound by theory, with this invention it is now known that pAMPK is elevated after ischemic stroke in a focal reperfusion model in mice. AMPK is elevated within 90 min of ischemic insult, and increases four-fold during early reperfusion. With this invention it is also now known that, administration of AMPK inhibitors not only resulted in decreased activation of AMPK (as shown by decreased phosphorylation of AMPK), but also provided significant neuroprotection. It has also been found that administration of AMPK activators can exacerbate stroke damage.

While not wishing to be bound by theory, it is thought that AMPK, in addition to playing a major role in physiological energy regulation, has far-reaching effects on cellular survival after ischemic stress. During ischemic stress energy demand is high, yet energy supply is low due to the lack of substrate (oxygen and glucose). By interfering with cellular energy perception and AMPK activation; the ischemic threshold of the cells may be augmented, allowing cells to survive in ah energy deficient but quiescent state until energy production can be restored. Modulation of metabolic pathways with synthetic FAS inhibitors/CPT-1 stimulators, such as C75, can alter neuronal metabolism, and create a positive energy balance. C75 inhibits AMPK in both cortical cultures and the hypothalamus in vivo, indicating that AMPK is responsive to neuronal energy balance. C75 administration leads to sustained increases in neuronal ATP levels in cultured neurons. Under ischemic conditions continued ATP depletion may exceed energy restorative pathways, leading to an inability of the cell to die by the energy-consuming process of apoptosis, shunting cells into necrotic cell death. Thus, sensing ATP levels may be important in neuronal responses to ischemia and AMPK inhibitors may ATP and the neurons.

AMPK activation occurs after cerebral ischemia; in this setting, its activation is detrimental to neuronal survival. AMPK localized to neurons, and retained this pattern of distribution (as opposed to glial localization) in the post-ischemic brain. AMPK was activated rapidly, within 90 minutes of vessel occlusion in vivo, and within 2 hours after oxygen glucose deprivation (OGD) in vitro. Increased levels of AMPK were seen throughout the brain, in both penumbral areas as well as in areas far removed from the ischemic insult Initially, this increase was thought to represent an adaptive response to neuronal stress, as a mechanism whereby the brain could increase ATP production in times of increased energy demand. Surprisingly, however, our pharmacological studies clearly demonstrate that inhibition of AMPK activation under conditions of neuronal ischemia reduced stroke damage. Administration of the AMPK inhibitor compound C, or the FAS inhibitor C75, provided significant neuroprotection in our model. In contrast, administration of the AMPK activator AICAR exacerbated stroke damage. Lastly, nNOS deficient mice had both smaller infarcts and lower pAMPK levels after stroke, whereas mice deficient in PARP-1 had similar AMPK levels to WT despite smaller infarcts. This suggests that the nNOS and ONOO pathways are important activators of AMPK in vivo under conditions of neuronal stress. Activation of neuronal AMPK is detrimental in an in vivo model of ischemia and reperfusion injury and that prevention of stroke-induced phosphorylation of AMPK is neuroprotective.

One well-characterized cytotoxin formed in ischemic cells is peroxynitrite (ONOO), a potent oxidant by-product formed when superoxide and NO are produced at near equimolar amounts. There is a constant leak of superoxide from the mitochondrial respiratory chain, which is deactivated by endogenous antioxidants, such as superoxide dismutase (SOD). Under conditions of increased NO production, NO can out-compete SOD for superoxide resulting in ONOO formation. ONOO irreversibly inhibits enzymes, damages DNA, and activates the energy consuming, NAD-depleting DNA repair enzyme poly(ADP-ribose) polymerase (PARP-1). Exposure of bovine endothelial cells to chemically synthesized ONOO activated AMPK without a change in AMP concentration, an effect replicated with hypoxia/re-oxygenation. These effects were ameliorated by adenoviral overexpression of SOD or administration of NOS inhibitors suggesting that ONOO mediated AMPK activation is mediated by NO. Recently, it was found that the anti-diabetic drug Metformin can also activate AMPK independently of AMP levels by a similar mechanism. This suggests that the NO/ONOO pathway may be an important stimulus for AMPK activation. Our studies in nNOS−/− mice support tins hypothesis, as reductions in NO and ONOO formation seen in these animals led to a dramatic reduction in stroke-induced AMPK activation. However, male nNOS mice have significantly smaller strokes than their WT counterparts. It is possible that any manipulation mat reduces ischemic damage would result in a decrease in pAMPK activation due to the "milder" ischemic stress placed on the brain. Elevations in AMPK could simply represent a marker of increased ischemic damage. We addressed these questions by examining pAMPK levels in male mice with targeted deletion of PARP-1. Surprisingly, PARP-1 null mice had an equivalent rise in stroke-induced pAMPK compared to their WT despite significantly smaller (>50%) infarcts. This suggests that pAMPK elevation is not simply a marker of increased ischemic damage but may be mechanistically related to ONOO and nNOS.

The consequences of AMPK activation to cell survival after ischemic insults in vivo were previously unknown. The majority of work has been done in vitro, often with transformed cell lines. AMPK activation with AICAR enhanced survival under conditions of reduced energy availability (glucose deprivation and glutamate excitotoxicity) in cultured hippocampal neurons. However, numerous investigators have now documented a pro-apoptotic effect of AICAR on numerous cell lines, including hepatocytes, neuroblastoma cells, and mouse MMIN cells through stimulation of c-jun-N-terminal kinase (JNK), c-myc and capsase 3. In contrast, AICAR is protective in ischemic cardiomyocytes and prevents ceramide-induced astrocytic apoptosis suggesting that the effects of AICAR are dependent on both the cell type and model system used. AICAR is taken up info the cell and accumulates in the cytoplasm as the mdnophosphorylated nucleotide, ZMP, which mimics the effects of AMP and activates AMPK without altering cellular ATP levels. However, AICAR is non-specific, and has numerous other effects in the cell, including induction of adenosine, a known vasodilator via competition for nucleoside transport AICAR reduced delayed cell death in the hippocampus after global ischemia in gerbils, but in this case AICAR was utilized an adenosine activator. In addition, the model of ischemic insult is quite different than our ischemia-reperfusion injury.

Our data demonstrate that activation of AMPK occurs in stroke, and that this response, when augmented by AICAR, exacerbates tissue damage. A limitation to the use of AICAR in in vivo studies was demonstrated by our physiological data, which revealed a transient, yet significant drop in MAP in AICAR-treated mice. The reduction in MAP may have increased infarction independently of effects on AMPK by a decrease in perfusion of peri-infarct areas. Given the brevity of the drop, the maintenance of CBF (via LDF (laser doppler flow)), and the dramatic neuroprotection seen with pharmacological inhibition of AMPK, this is unlikely to be the primary explanation. In addition, recent data suggests that AMPK activation is also detrimental to the ischemic heart as cardiac injury induced by $H_2O_2$ was partially ameliorated by treatment with Compound C similar to our findings in the CNS.

Whereas activation of AMPK may be beneficial in some peripheral tissues in response to hypoxia, the situation in the CNS may be different. For example, in hypoxic endothelial cells, eNOS is activated by direct phosphorylation by AMPK to presumably alter vascular tone to enhance blood flow However, in stroke, this presumably beneficial effect of AMPK may be of limited use, as cerebral blood flow (CBF) is severely reduced during the acute occlusion (by the filament), making eNOS-induced vasodilation a futile, energy consumptive process. In addition, under hypoxic conditions enhanced NO production (via eNOS) can lead to increased levels of ONOO propagating free radical injury.

Examination of both in vivo and in vitro systems is crucial in determining the physiological outcome of AMPK activation. The severe ATP-depleting effects of excessive NO exposure in neurons in vitro is mediated by both an inhibitory effect on mitochondrial respiration as well as inhibition of glycolysis, which leads to reductions in both oxidative and glycolytic energy production. However, in astrocytes, NO-induced inhibition of respiration leads to an increase in astrocytic glycolysis with a reduction in apoptosis. This rapid NO-dependent activation of astrocytic glycolysis is mediated by AMPK activation with subsequent activation of phosphofructo-2-kinase (PFK-2). Astrocytes therefore respond to stress and hypoxia with a compensatory increase in, glycolysis, providing energy and preventing cell death. Transaction of astrocytes with AMPK siRNA renders astrocytes unable to increase glycolysis in response to NO, and increased levels of apoptosis. Neurons, unlike astrocytes, lack the enzymatic machinery to enhance glycolysis, as they have very low levels of PFK2 and restricted capacity for fatty acid oxidation. Therefore, activation of AMPK under pathological conditions such as stroke may not enhance neuronal survival.

Although focal stroke involves a discrete area of brain, compensatory mechanisms including changes in cerebral blood flow (CBF) and metabolic demand occur in areas far removed from the ischemic "core". For example, cerebral edema is seen in the contralateral "unaffected" hemisphere after large unilateral focal lesions, suggesting that brain water content can vary in areas remote from the original injury. Communication with non-ischemic brain can occur through transcallosal or intrahemispheric "diaschisis", leading to impairments in CBF, electrophysiological activity, and metabolism. It is likely that the signal for AMPK activation is transmitted globally throughout the brain as is suggested by the robust contralateral rise in pAMPK levels.

Activation of AMPK increases stress in already compromised neurons. Interfering with cellular energy perception may augment the ischemic threshold, allowing cells to survive in energy deficient but quiescent state until energy production can be restored. Reducing AMPK activation could encourage "neuronal hibernation" early in the ischemic cascade, preventing complete neuronal energy failure, prolonging neuronal viability until blood and nutrient supply can be restored. Improving energy dynamics in ischemic neurons allows for the possibility of prolonging the "therapeutic window" in clinical stroke. The suggestion that neuronal metabolic pathways may represent an important and novel target for neuroprotection is demonstrated by our findings.

The invention is further described by the following non-limitative examples:

EXAMPLES

Experimental Animals

The following experiments were conducted in accordance with NIH guidelines for the care and use of animals in research and under protocols approved by the Animal Care and Use Committee of the Johns Hopkins University.

Ischemic Model

Cerebral ischemia was induced by 120 minutes of reversible right middle cerebral artery occlusion (MCAO) under halothane anesthesia followed by reperfusion for various times for male C57B6 mice (Charles River) or male rats, as described by McCullough, et al., Stroke, 32, 796-802 (2001) and McCullough, et al., J. Neuroscience, 24, pp. 257-268 (2004), respectively. Intra-ischemic and 22 hour post-reperfusion neurological deficits (NDS) were scored as follows: 0, no deficit; 1, forelimb weakness and torso turning to the ipsilateral side when held by tail; 2, circling to affected side; 3, unable to bear weight on affected side; and 4, no spontaneous locomotor activity or barrel rolling. Any animal without deficit was excluded from the study. At end-ischemia, the animal was briefly re-anaesthetized and reperfusion was initiated by filament withdrawal. Sham animals were subjected to the equivalent surgical preparation, but the suture was not advanced into the internal carotid. For the pharmacological neuroprotection studies, mice survived 22 hours after reperfusion, at which time behavioral scoring was done. The brain was then harvested for pathological examination with TTC histology (see Histopathology section). In separate animal cohorts, physiological measurements, femoral arterial blood pressure and cortical perfusion (laser Doppler flowmetry) were evaluated throughout MCAO and early reperfusion as described in the 2001 McCullough paper referenced above. Additional animals were exposed to ischemia or sham surgery after pharmacological or vehicle treatment and were sacrificed at 4 or 24 hours for Western blot analysis. Male nNOS and PARP-1 deficient mice (see, Huang, et al., Science, 265, 1883-1885 (1994); Eliasson, et al, Nat. Med, 3, 1089-1095 (1997)) were subjected to 2-hour right MCAO or sham surgery and compared to additional WT cohorts (C57-BL6 for nNOS−/− and SVEV for PARP−/−).

Terminal Histopatholosy

Infarction volume was analyzed by 2,3,5-triphenyltetrazolium staining in five 2-mm slices. Infarction volume was determined by video microscopy and image analysis (Inquiry 3, Loats Associates), as previously described by McCullough, et al., *J. Neuroscience* 23, pp. 8701-8705 (2003).

Western Blot Analysis

Mouse and rat stroke and sham brain samples were obtained by rapid removal of the brain from the skulk resection of the cerebellum, followed by immediate dissection into the right (R) and left (L) hemispheres. Samples were flash frozen in liquid nitrogen. Samples from rats were further sub-dissected into core and penumbral regions for both hemispheres. Samples were stored at −80° C. until use. Each sample was homogenized in 200 µl of lysis buffer (50 mM Tris-HCl, pH 7.5, 250 mM sucrose, 5 mM sodium pyrophosphate, 50 mM NaF, 1 mM EDTA, 1 mM EGTA, 1 mM DTT, 0.5 mM PMSF, 0.1 mM benzamidine, 50 µg/ml leupeptin, 50 µg/ml soybean trypsin inhibitor). SDS detergent was added to a final concentration of 0.2%, and lysates were boiled for 5 min. After the supernatant was harvested, protein concentration was determined using a BCA kit (Bio Rad). 40 µg of protein was loaded per lane on a 4-15% gradient SDS-polyacrylamide gel, and transferred to a polyvinylidene difluoride membrane. Blots were successively probed, stripped and reprobed for antigen detection.

Phosphorylation of AMPKα was determined using an anti-phospho-AMPKα (α1 and α2 Thr) antibody (1:1000, Cell Signaling). ACC (1:500), p-ACC (1:1000), pAkt (1:500), and Akt (1:500) antibodies were obtained from Upstate, Lake Placid, N.Y. Anti-AMPKα antibody (anti-α1 and α2, 1:1000; Cell Signaling), hsp-70 (1:1000; Santa Cruz), and β-actin (1:5000; Sigma) were used as loading controls. All blots were incubated overnight in primary antibody at 4° C. in TBS buffer containing 5% BSA and 0.1% Triton-X-100. The secondary antibody (goat anti-rabbit IgG, Chemicon) was diluted to 1:5,000, and ECL (pico) detection kit was used for signal detection.

Immunohistochemistry

Floating brain sections were prepared as described by Kim, et al., *J. Biol. Chem.*, 279, 19970-19976 (2004) with modifications. Free-floating sections were blocked in PBS containing 5% goat serum, 1 mg/ml BSA, 0.05% Triton-X100, and 1 mM NaF for 1 hr at room temperature followed by incubation with anti-phospho-AMPKα antibody (1:100), GFAP (1:1000, DAKO; for astrocytes), NeuN (Chemicon 1:100; a marker for mature neurons) or VWF (Santa Cruz; 1:400 for endothelial cells), in PBS containing 1% goat serum, 1 mg/ml BSA, 0.05% Triton-X-100, 1 mM NaF overnight at 4° C. The secondary antibody (1:200; Vector Laboratories; Burlingame, Calif.) was incubated in PBS containing 1% goat serum for 1 hr 30 min (Texas Red, FITC). The signal was visualized with immunofluorescence confocal microscopy using Zeiss image acquisition software (Zeiss LSM 510).

Hippocampal Slice Culture and OGD

Hippocampal organotypic slice cultures were prepared as described by McCullough, et al., *Stroke,* 32, 796-802 (2001). Coronal hemispheric slices of 350 microns were derived from postnatal day 7 rat pups using a tissue chopper (McILwain tissue chopper; Vibratome Company, St. Louis, Mo.). Hippocampal slices were transferred onto 30 mm Millicell permeable membrane inserts (0.4 µm; Millipore, Bedford, Mass.), in six well plates, with each well containing 1 ml of medium (50% MEM, 25% HBSS, 25% heat-inactivated horse serum, 6.5 mg/ml D-glucose, 5 U/ml penicillin G, and 5 µg/ml streptomycin sulfate). Cultures were maintained in a humidified incubator under 5% $CO_2$ at 37° C. for 13 days. A complete medium change was performed twice a week. Induction of anoxia was performed at 13 d in vitro. Slice cultures were rinsed twice with warm BSS (in mM: 125 NaCl, 5 KCl, 1.2 $NaH_2PO_4$, 26 $NaHCO_3$, 1.8 $CaCl_2$, 0.9 $MgCl_2$, 10 HEPES, and 10 glucose), and returned to the incubator to equilibrate for 30 min. Slice cultures were rinsed twice with warm deoxygenated glucose-free BSS, transferred to an air-tight chamber, flushed with anoxic gas (5% $CO_2$, 85% $N_2$, and 10% $H_2$), and maintained at 37° C. for 60 min. Controls were rinsed with BSS and transferred to a normal aerated incubator for 1 hr. The period of anoxia was terminated by returning the cultures to fresh medium (50% MEM, 25% HBSS, 25% heat-inactivated horse serum, 6.5 mg/ml D-glucose, 5 U/ml penicillin G, and 5 µg/ml streptomycin sulfate) and samples were prepared for western analysis at 2, 4, 6 and 24 hours (as above). Control and OGD-treated slices were included in each experiment with triplicate wells or 15 slices per condition for each experimental group.

Statistical Analysis

All data are expressed as mean±SEM. Physiological variables and histology were analyzed by 1-way ANOVA with a post-hoc Newman-Keuls to correct for multiple comparisons. Post-ischemic neurological scores were analyzed by the Mann-Whitney U test. Values were considered statistically significant at *, $p<0.05$; , $p<0.01$; *, $p<0.001$ Results AMPK is Expressed in Neurons Post-Ischemia Brain tissue sections obtained from mice subjected to 2 hours of MCAO followed by 2 hours of reperfusion showed prominent neuronal staining for both AMPK and pAMPK (FIG. 1, n=5/gp). They were also stained with NeuN (for mature neurons), GFAP (for astrocytes). Confocal microscopy demonstrates co-localization of NeuN and AMPK/pAMPK, with absent co-lacalization in astrocytes.

Figure 2:
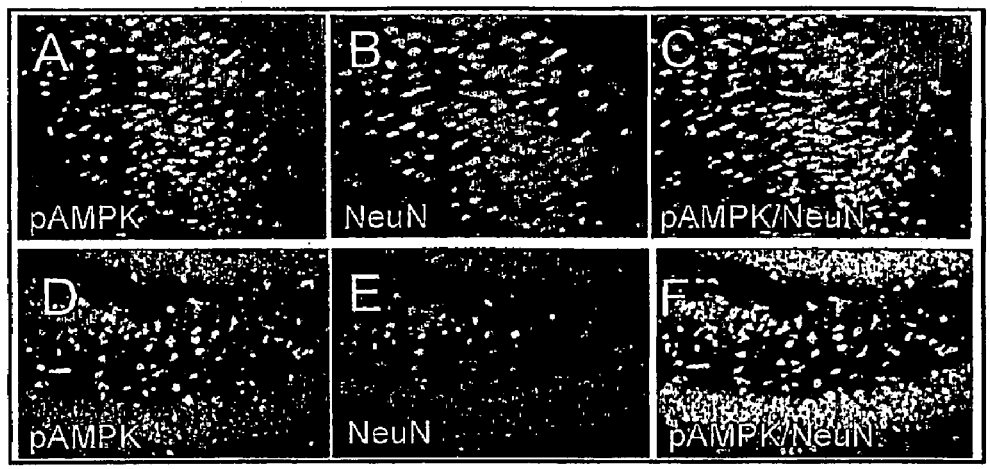
FIG. 2—Immunohistochemical localization of PAMPK and NeuN in ischemic mouse cortex and hippocampus.

Confocal microscopy demonstrated that AMPK (FIGS. 1A-C) and pAMPK (FIGS. D-F) localized to cortical neurons in the middle cerebral artery (MCA) distribution, as shown by double labeling immunofluorescence using the mature neuronal marker NeuN. Higher magnification of cortical neurons immunostained for NeuN and pAMPK (FIGS. 1 G-I) shows nuclear and cytoplasmic immunostaining for the α isoform. While AMPK may be only minimally expressed in non stimulated astrocytes in intact brain, previous studies have found AMPK immunoreactivity in cultured astrocytes. To clarify the localization of AMPK and pAMPK in vivo, we examined both normal non-ischemic tissue as well as brains harvested both 4 and 24 hours after infarction (at 2 or 22 hours of reperfusion) to determine whether AMPK is expressed in astrocytes after stroke. There was only minimal co-localization of GFAP with AMPK or pAMPK 4 hours after MCAO (FIGS. 1J-L and FIGS. 1M-O, respectively). Similar to 4-hour tissue, no co-localization of AMPK or pAMPK with GFAP was seen in cortex 24 hours after stroke (FIGS. 1P-R). In addition, no co-labeling of either AMPK or pAMPK with the endothelial marker von Willebrand factor (VWF) was seen in intact or ischemic brain (data not shown). To determine if this pattern of pAMPK immunolocalization was retained regionally, low power images of pAMPK and NeuN double labeling were obtained at 24 hours after infarction (22 hours of reperfusion) (FIG. 2). Similar levels of Staining were seen in both the cortex (FIGS. 2A-C) and the hippocampus (FIGS. 2D-F), with prominent pAMPK co-labeling with NeuN in both regions. No signal was seen in control sections without addition of primary antibody (data not shown). These results show that AMPK is expressed primarily in neurons in both the ischemic and non-ischemic brain, where it may function in a cell-autonomous manner to influence neuronal energy balance.

AMPK is Increased After MCAO

Male wild-type (WT) C57Bl6 mice were subjected to 2-hour right MCAO or sham surgery with varying reperfusion times. Physiological parameters, such as temperature, were held constant. There were no significant differences in physiological measurements between each treatment group compared to respective vehicle in C75 and Compound C (Cpd C) treated animals. MAP and LDF are shown averaged over the 2 hours of ischemia. AICAR treated animals had a significant reduction in MAP at 15 minutes (p<0.05), with no overall difference over 2 hours of monitoring. Reductions in intraischemic LDF were equivalent in Vehicle and AICAR animals, however there was a significant reduction (p<0.05) in LDF at 30 minutes of reperfusion (n=4/group):

although these were most notable at later time points (i.e., 6, 12 and 24 hours). β-actin served as a loading control. The global increase in pAMPK levels suggests that AMPK is activated secondary to metabolic derangements and compensatory responses not only in the ischemic area, but also in the contralateral nonischemic side.

AMPK is Activated After OGD in Vitro

Figure 4:
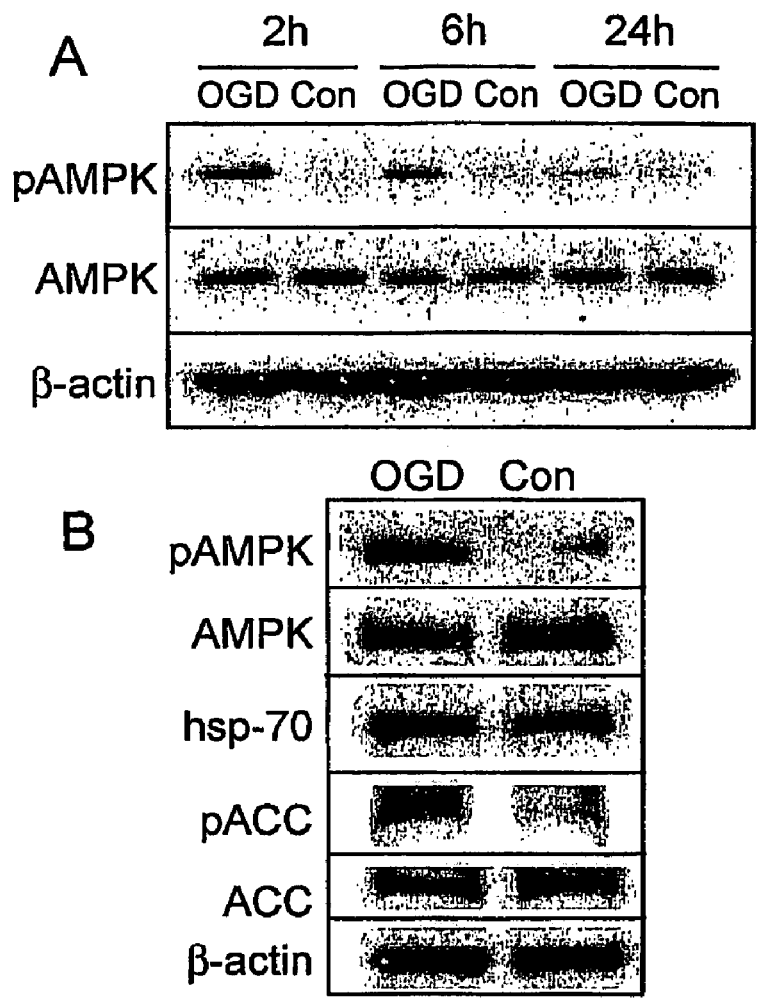
FIG. 4—Western blot analysis showing that AMPK phosphorylation is elevated after in vitro oxygen-glucose deprivation (OGD).

In addition to the in vivo findings, we also determined whether AMPK was activated in vitro in hippocampal slice cultures after oxygen-glucose deprivation (OGD) an in vitro model of stroke. We found a robust increase in pAMPK levels 2 hours after OGD compared to normoxic normoglycemic control cultures (FIG. 4A). This increase in pAMPK persisted at 6 hours, but normalized by 24 hours, as was seen in our in vivo studies. A downstream target of AMPK activation is acetyl-CoA carboxylase (ACC), which is the pace-setting enzyme in the de novo synthesis of fatty acids; when activated, AMPK mediates the phosphorylation of ACC, thus inactivating ACC, and limiting the anabolic process of fatty acid synthesis in times of energy deficiency. Evaluation of slice samples 4 hours following OGD demonstrated an increase in the level of phosphorylated or inactivated acetyl-CoA carboxylase (pACC) (FIG. 4B), supporting the idea that the observed increases in pAMPK are physiologically relevant Total AMPK and ACC levels changed minimally at all examined time-points in both OGD or control slices.

AMPK Elevation is Seen in the Ischemic Penumbra

Figure 5:
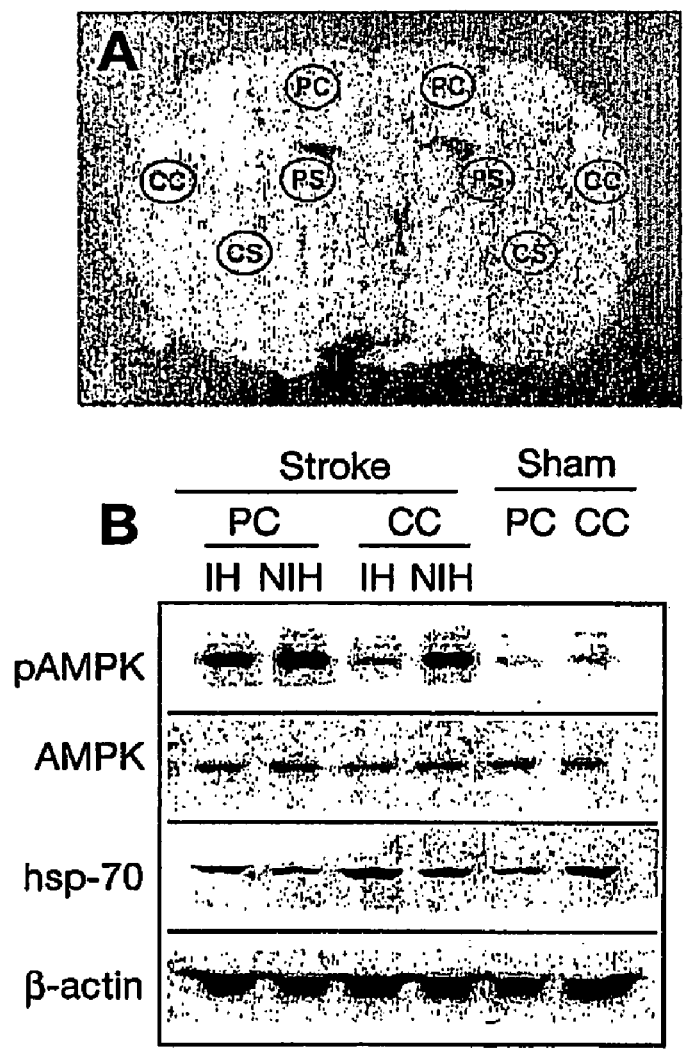
FIG. 5—TTC staining and Western blot analysis shows the pAMPK is elevated in the ischemic and non-ischemic brain hemispheres.

Assuming mat metabolic derangements in stroke may be more severe in the necrotic core of an infarct, whereas pro-survival pathways may be activated in the penumbra in an attempt to salvage marginally functioning brain, we dissected out core (CC) and penumbral (PC) tissues from both the ischemic right hemisphere (TH, ischemic hemisphere) or non-ischemic left hemisphere (NIH; non-ischemic hemisphere) for Western blot analysis from rat brains (n=6/group) 6 hours after stroke (FIG. 5). Rats were used for this experiment, as dissection of core and penumbra is more rapidly and

TABLE 1

INTRA-ISCHEMIC PHYSIOLOGICAL VARIABLES AND LASER DOPPLER FLOW (LDF) VALUES IN EACH OF THE EXPERIMENTAL GROUPS

| Parameter | Vehicle | Cmpd C | Vehicle | C75 | Vehicle | AICAR |
|---|---|---|---|---|---|---|
| Ph | 7.37 ± 0.05 | 7.36 ± 0.07 | 7.30 ± 0.10 | 7.34 ± 0.08 | 7.37 ± 0.05 | 7.33 ± 0.11 |
| $PCO_2$ | 45.2 ± 2.8 | 42.1 ± 3.1 | 47.2 ± 4.7 | 47 ± 7.1 | 42 ± 3.6 | 39.7 ± 4.9 |
| $PO_2$ | 140 ± 9.8 | 144.6 ± 14.3 | 144.7 ± 11.6 | 135 ± 14.2 | 147 ± 15.9 | 128 ± 15.2 |
| MAP | 80.7 ± 4.8 | 82.2 ± 5.9 | 81.5 ± 3.9 | 79.1 ± 6.5 | 84 ± 7.1 @15 | 69 ± 12.4@15 |
| | | | | | 81.6 ± 4.4 (all) | 77.7 ± 7.3 (all) |
| Hg | 13.6 ± 1.9 | 12.7 ± 1.3 | 13.8 ± 1.8 | 12.9 ± 0.5 | 13.8 ± 2.3 | 13.4 ± 0.9 |
| $HCO_3$ | 23.5 ± 1.1 | 23.1 ± 0.08 | 22.6 ± 2.4 | 22.8 ± 1.2 | 23.6 ± 2.6 | 22.9 ± 2.3 |
| LDF | 9.8 ± 1 | 10.6 ± 0.9 | 10 ± 1.3 | 10.6 ± 0.88 | 11.3 ± .8 | 11.1 ± 1.2 |
| (% BL) | | | | | RP 98 ± 5.3 | RP 83 ± 10.8 |

Figure 3:
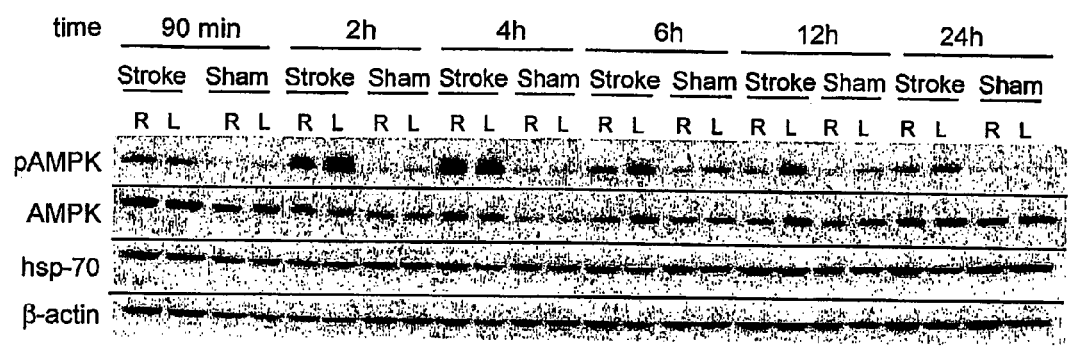
FIG. 3—Time course of elevation of pAMPK after stroke.

As can be seen in FIG. 3, pAMPK (as detected by a panα subunit antibody to Thr phosphorylation site (see, Hawley, et al., *J Biol Chem* 271, 27879-27887 (1996)) was elevated in ischemic brain (Stroke) as early as 90 minutes following ischemia compared to animals that had undergone sham surgery (Sham) (n=6 per time point for ischemic animals; 4 per time point sham operated controls). pAMPK levels were elevated in the right, ischemic hemisphere (R) and on the left, non-ischemic hemisphere (L), and remained elevated for 24 hours (22 hours of reperfusion) in both the ischemic right and the non-ischemic left hemispheres. In contrast, pAMPK levels in sham brains remained stable over the 24-hour period. Total AMPK levels showed minimal changes. Appropriate elevations of hsp-70 were seen in the ischemic hemisphere reliably done using the larger rat brain; this also allowed us to confirm our findings in a different species. The areas of ischemia and of dissection were visualized using TTC staining at 24 hours (FIG. 5A). pAMPK levels were dramatically elevated in the cortical penumbral non-ischemic hemisphere and in the contralateral non-ischemic hemisphere (PC NIH and CC NIH, respectively), compared to pAMPK levels in either hemisphere in the sham brain (PC and CC) (FIG. 5B). pAMPK levels in the ischemic core (CC in the ischemic hemisphere) were lower than in the other areas of brain, but were elevated compared to surgical shams (Sham CC and PC).

It is possible that the lower level of AMPK in the core represents failure of protein synthesis and energy-dependent phosphorylation in the ischemic core of the infarct However, expected increases in heat-shock protein 70 (see, Kury, et al., *Eur J Neurosci* 19, 1708-1720 (2004)) were seen. Alternatively, AMPK activation could represent a compensatory protective pathway in the penumbra. pAMPK could be up-regulated in neurons that are damaged, but remain viable, as a strategy to increase available energy supply. The rise in contralateral AMPK suggests that neurons far removed from the area of the insult may also be receiving a signal to increase energy availability. Therefore, increases in pAMPK levels and thus activity could represent an adaptive, endogenous neuroprotective pathway. To address this issue, we proceeded to pharmacologically manipulate AMPK levels to determine the effect of changing pAMPK levels to stroke outcome.

Compound C Reduces pAMPK Levels and is Neuroprotective

Figure 6:
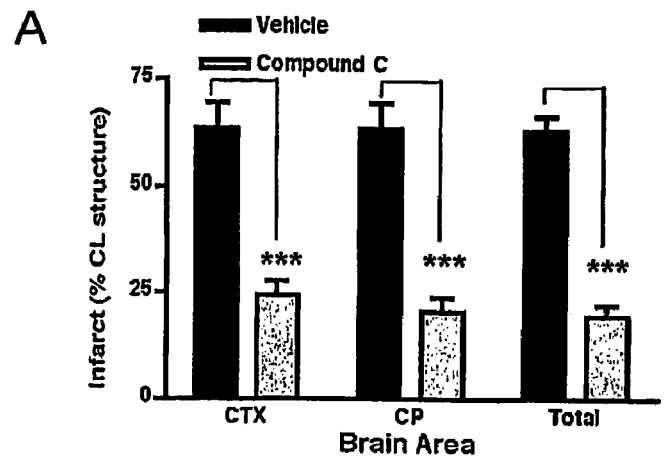
FIG. 6—Compound C treatment causes a significant decrease in regional and total stroke volume.
Figure 6:
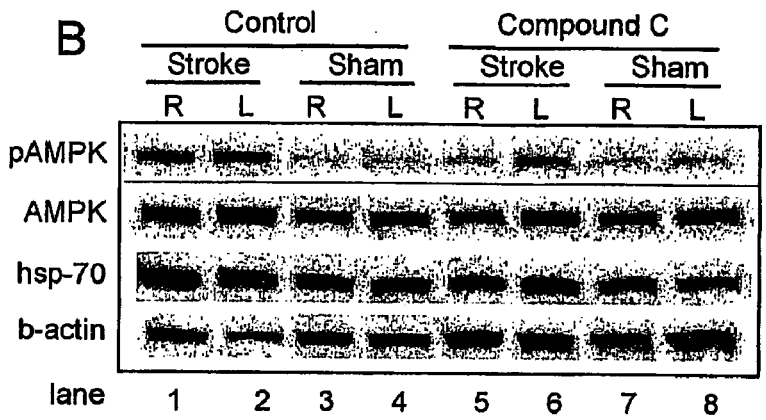
Figure 6:
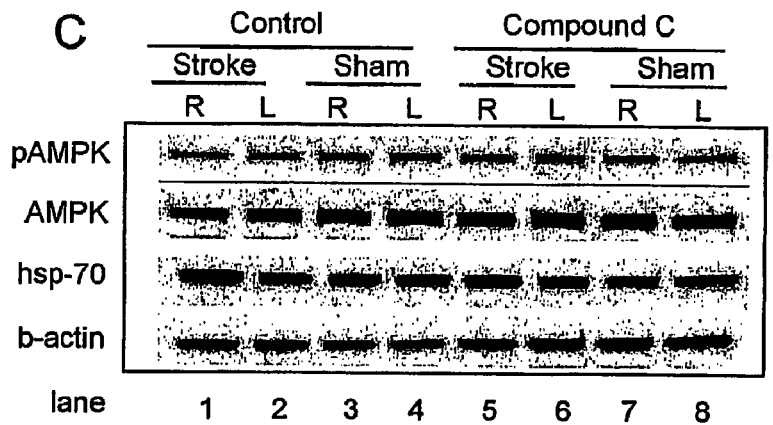

To examine the functional effects of AMPK activation in this ischemic model, we explored the effect of stroke outcome in mice treated with compound C, a pharmacological AMPK inhibitor described in *J. Clin Invest* 108, pp. 1167-1174 (2001). The effect on stroke outcome in animals treated with Compound C (20 mg/kg delivered intraperitoneally; n=14) or vehicle (n=8) at stroke onset (2-hr MCAO with 22 hr reperfusion) was determined (FIG. 6). Compound C significantly reduced total infarct volume (as measured by % non-ischemic hemisphere, corrected for edema using TTC), as well as striatal (CP; 64±5.7 vs. 21±3.9; p>0.001) and cortical (CTX; 63±3.4 vs. 19.4±3.3; p<0.001) infarct volumes compared to vehicle treated animals (FIG. 6A). A reduction in severity of behavioral deficits at 24 hours reflected these differences (vehicle 3.3±0.3 vs. compound C 1.9±0.2, p< 0.01). There was no difference in relative cerebral blood flow (CBF) as measured by laser Doppler, either during the intraischemic period (vehicle=9.8±0.54 vs. compound C=10.6±0.9; % of baseline; p=n.s.), or during the 30 minutes after reperfusion, suggesting that differences in-blood flow could not account for the differences in ischemic damage. No differences in physiological measurements were seen between treatment groups (Table 1) demonstrating the equivalent contribution of these factors to stroke outcome.

Additional groups of vehicle or compound C treated mice subjected to either 2 hours MCAO (n=6/group) or sham surgery (n=4/group) were sacrificed 4 hr (FIG. 6B) or 24 hr (FIG. 6C) after infarction for determination of AMPK and pAMPK levels. Lysates from either the ischemic (right, R) or non-ischemic (left, L) hemispheres were analyzed by Western blot analysis in both stroke and sham surgery animals. The anticipated increase in pAMPK 4 hr after infarction (2 hours of reperfusion) was seen in vehicle treated animals (FIG. 6B, lanes 1 and 2) relative to sham animals (lanes 3 and 4), but the levels of pAMPK were reduced in compound C treated animals (lanes 5 and 6); total AMPK levels were unchanged. The effect of compound C was transient; pAMPK levels were similar to that seen in vehicle-treated mice by 24 hr (FIG. 6C, lanes 1 and 2 compared to lanes 5 and 6). These results suggest that the inhibition of AMPK with compound C is neuroprotective, and that this neuroprotective effect correlates with a reduction in pAMPK levels.

Reduction in pAMPK Levels by the FAS Inhibitor C75 is Neuroprotective in Stroke.

Figure 7:
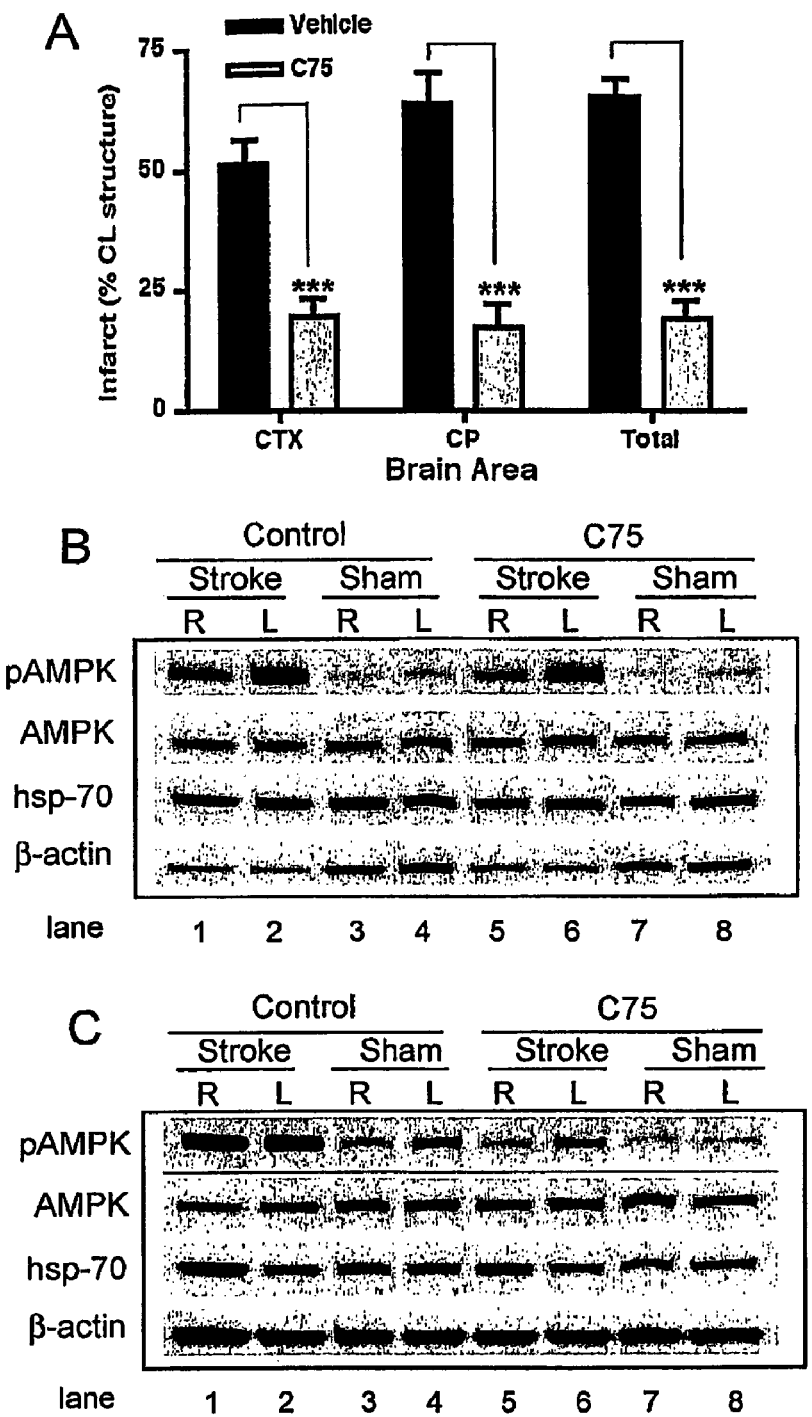
FIG. 7—Administration of C75 leads to significant neuroprotection

We administered the FAS inhibitor C75 (20 mg/kg i.p.) or vehicle (RPMI) immediately prior to the onset of ischemia (n=9/gp). We based this dose on previous in vivo data that demonstrated an effect on feeding behavior and an inhibition of C75 activity in hypothalamus. There was a significant reduction in total and regional infarction volume seen in the C75-treated group (p<. 001). Improvements in behavioral scores were seen (vehicle 3.2±0.05 vs. C75 2.0±0.03, p<0.01). As with compound C, no differences in LDF or physiological variables were seen (n=4). Additional groups of vehicle or C75 treated mice subjected to either 2-hour MCAO and reperfusion (n=6/group) or sham surgery (n=4/group) were sacrificed 4 hr (FIG. 7B) or 24 hr (FIG. 7C) following stroke for analysis of AMPK and pAMPK levels. The anticipated increase in pAMPK at 2 hr of reperfusion was seen in both and C75-treated vehicle-treated mice (FIG. 7B, lanes 1 and 2 vs. lanes 5 and 6, respectively), although the increase in pAMPK levels was blunted by C75 treatment. As with compound C, the reduction in the increase in pAMPK levels was more pronounced in the ischemic right hemisphere (R) compared to the non-ischemic left hemisphere (L). Compared to vehicle-treated mice, C75 reduced pAMPK levels in both sham and stroke mice prominently 24 hr following stroke (FIG. 7C, lanes 1-4 vs. lanes 5-8, respectively), indicating a more lasting central effect of C75 (compared to compound C) in reducing pAMPK levels.

As shown in FIG. 5A, there was a significant reduction in total and regional infarction volume seen in the C75-treated group (P<0.001). There were no significant differences in intra-ischemic or reperfusion blood flow blood flow as measured by laser Doppler nor were there any differences seen in MAP, pH or blood gas measurements in the non-survival cohort (n=4, data not shown). Additional groups of vehicle or C75 treated mice subjected to either 2-hour MCAO (n=6/gp) or sham surgery (n=4/gp) were sacrificed at 4 hr (FIG. 5B) or 24 hr (FIG. 5C) after stroke for analysis of AMPK and pAMPK levels. The anticipated increase in pAMPK at 2 hr of reperfusion was seen in vehicle and C75-treated mice. Reductions in pAMPK levels were seen in C75 treated animals at 24 hrs in both sham and stroke mice, documenting the more lasting central effect of C75 (compared to compound C) in reducing pAMPK.

AMPK Activation with the AMPK Activator 5-Ammoimidazole-4-Carboxamide Ribonucleoside (AICAR) Exacerbates Stroke.

Figure 8:
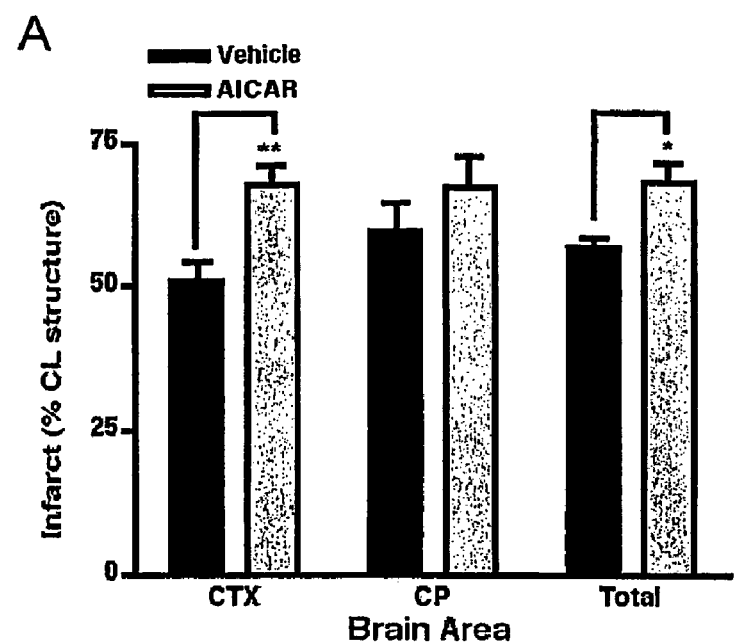
FIG. 8—Administration of AICAR, an AMPK activator, exacerbates stroke.
Figure 8:
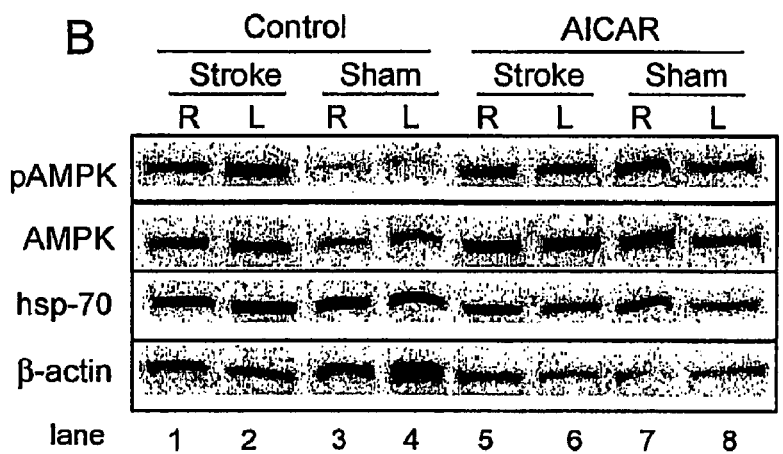

The widely used AMPK activator, 5-aminoimidazole-4-carboxamide ribonucleoside (AICAR), (see, Corton, et al., *Eur J Biochem*, 229, 558-565 (1995)) was administered at stroke onset (500 mg/kg i.p.; n=11/group). AICAR is taken up into cells and phosphorylated to form ZMP, which mimics the effects of AMP on AMPK activation. There was a significant exacerbation of total and cortical (CTX) stroke volumes in AICAR-treated animals (FIG. 8A). Physiological monitoring demonstrated a significant drop in mean arterial pressure (MAP) in AICAR treated animals that self-corrected by 15 minutes after injection (MAP vehicle 84 vs. AICAR 69 mmHg, p<0.05). There were no differences in intraischemic CBF, but a reduction in CBF was seen in AICAR-treated mice compared to controls at 30 minutes after reperfusion (98 vs. 82.7% of baseline, p<0.05). This suggests that part of the detrimental effects of AICAR may be secondary to decreased perfusion pressure, in addition to its effects on AMPK. Western blot analysis showed elevations of pAMPK 4 hr following stroke (2 hours of reperfusion) in AICAR treated vs. vehicle treated animals (FIG. 8B lanes 5-8 vs. lanes 1-4, respectively), which returned to baseline by 24 hr (data not shown).

Loss of nNOS Prevents Stroke-Induced Elevations in pAMPK

Figure 9:
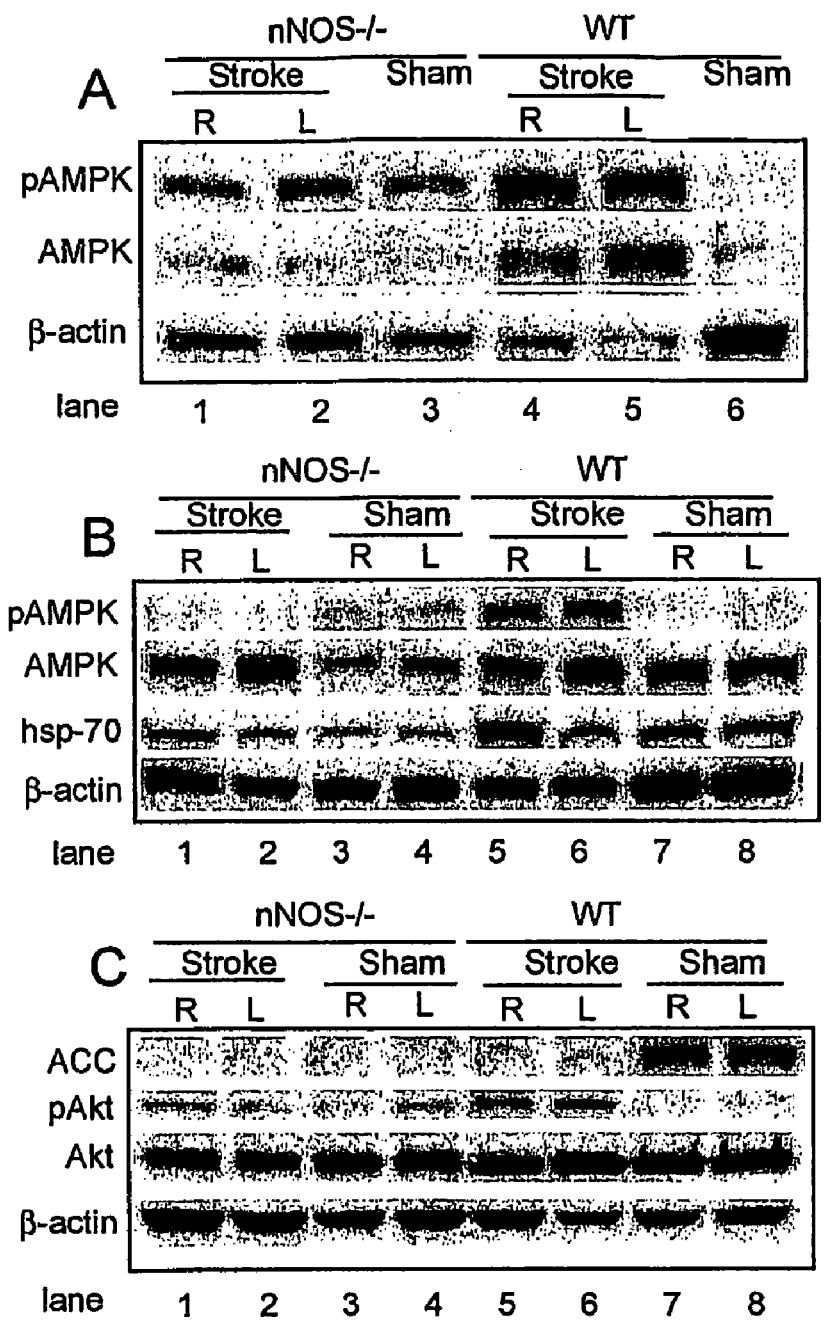
FIG. 9—AMPK and pAMPK levels in wild type (WT) and neuronal nitric oxide synthase deficient mice (nNOS-/-).

As ONOO (peroxynitrite) is a significant contributor to stroke-induced neuronal damage, and AMPK is activated by ONOO as well as hypoxia in vitro, we evaluated the role of neuronal NOS (nNOS) in AMPK activation after stroke (FIG. 9). nNOS knockout animals have significantly smaller infarcts than their wild-type counterparts, primarily due to a reduction in ONOO production. We confirmed the neuroprotective effect of nNOS deletion in our MCAO model (total infarct: 55.8±4.9% in WT; 31.9±4% in nNOS−/−; p<0.01). Male nNOS−/− and wild type (WT) mice were subjected to right MCAO, and brains were harvested at either 4 hr (FIG. 9A) or 24 hr (FIG. 9B) following infarction (22 hours of reperfusion). At 4 hr, WT mice showed an elevation in pAMPK compared to WT sham in both the ischemic (right, R) and non-ischemic (left, L) hemispheres. However, in nNOS−/− mice, the stroke-induced rise in pAMPK levels was abrogated, and pAMPK levels were similar to sham. Similar results were found at 24 hr (FIG. 9B). Levels of phosphorylated Akt were also decreased in nNOS−/− mice compared to WT at 24 hr after infarction (22 hours of reperfusion), suggesting a possible relationship between Akt, AMPK, and NOS (FIG. 9C).

Figure 10:
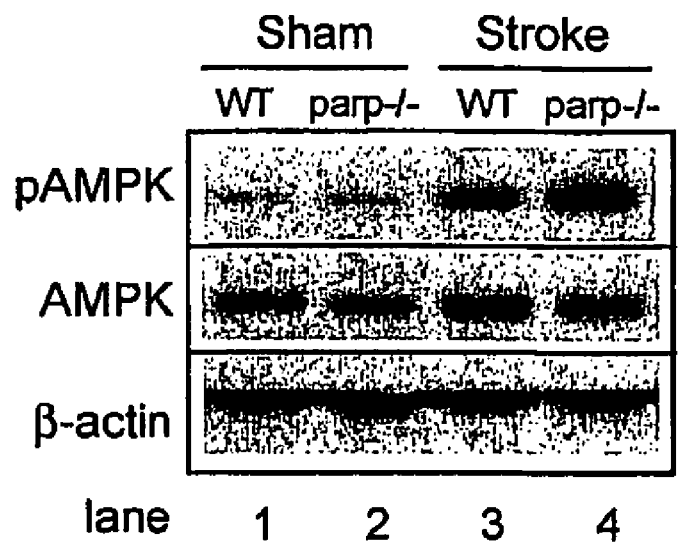
FIG. 10—AMPK and pAMPK levels in wild type (WT) and poly(ADP-ribose) polymerase (PARP-1) deficient mice

As the decreased activation of AMPK in nNOS−/− mice might simply be a reflection of the decreased ischemic damage seen in this strain, we also examined male mice deficient in the DNA repair enzyme Poly (ADP-ribose) polymerase-1 (PARP-1 knockout mice), which have similar reduction in stroke volumes to nNOS−/− male mice (FIG. 10). Surprisingly, PARP-1 deficient mice had similar levels of pAMPK activation in the ischemic hemisphere compared to their respective WT (FIG. 10, only ischemic hemisphere shown) despite smaller infarcts. This suggests that reductions in NO or ONOO production seen in nNOS deficient mice lead to the selective amelioration of AMPK activation.

We claim:

1. A method of neuroprotection in a subject who is experiencing or has experienced a stroke, or other interruption of cerebral blood flow by other etiologies, the method comprising: administering a neuroprotective amount of a compound to a subject in need thereof, wherein said compound is C75 or Compound C.

2. The method of claim 1, wherein said compound is C75.

3. The method of claim 1, wherein said compound is Compound C.

4. A method of neuroprotection in a subject who is experiencing or has experienced a stroke, or other interruption of cerebral blood flow by other etiologies, the method consisting essentially of: administering a neuroprotective amount of a compound to a subject in need thereof, wherein said compound is C75 or Compound C.

5. The method of claim 4, wherein said compound is C75.

6. The method of claim 4, wherein said compound is Compound C.

* * * * *